United States Patent
Bly et al.

(10) Patent No.: US 7,747,334 B2
(45) Date of Patent: Jun. 29, 2010

(54) LEFT VENTRICULAR LEAD SHAPES

(75) Inventors: Mark J. Bly, Falcon Heights, MN (US);
Brian D. Soltis, St. Paul, MN (US);
Bruce A. Tockman, Scandia, MN (US);
Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 807 days.

(21) Appl. No.: 11/277,326

(22) Filed: Mar. 23, 2006

(65) Prior Publication Data
US 2007/0225786 A1    Sep. 27, 2007

(51) Int. Cl.
*A61N 1/372* (2006.01)

(52) U.S. Cl. ..................... 607/122
(58) Field of Classification Search .......... 607/122; 604/508
See application file for complete search history.

(56) References Cited

U.S. PATENT DOCUMENTS

| | | | |
|---|---|---|---|
| 4,394,866 A | 7/1983 | Hughes | |
| 4,402,328 A | 9/1983 | Doring | |
| 4,402,330 A | 9/1983 | Lindemans | |
| 4,643,202 A | 2/1987 | Roche | |
| 5,387,233 A | 2/1995 | Alferness et al. | |
| 5,423,772 A | 6/1995 | Lurie et al. | |
| 5,423,865 A | 6/1995 | Bowald et al. | |
| 5,433,729 A | 7/1995 | Adams et al. | |
| 5,445,148 A | 8/1995 | Jaraczewski et al. | |
| 5,476,498 A | 12/1995 | Ayers | |
| 5,683,445 A | 11/1997 | Swoyer | |
| 5,800,495 A | 9/1998 | Machek et al. | |
| 5,807,324 A * | 9/1998 | Griffin, III | 604/529 |
| 5,925,073 A | 7/1999 | Chastain et al. | |
| 5,964,795 A | 10/1999 | McVenes et al. | |
| 5,991,668 A | 11/1999 | Leinders et al. | |
| 5,999,858 A | 12/1999 | Sommer et al. | |
| 6,070,104 A | 5/2000 | Hine et al. | |

(Continued)

FOREIGN PATENT DOCUMENTS

EP    0672434    9/1995

(Continued)

OTHER PUBLICATIONS

International Search Report and Written Opinion on International Application No. PCT/US2007/064820, filed Mar. 23, 2007, both mailed Sep. 24, 2007.

*Primary Examiner*—Carl H. Layno
*Assistant Examiner*—Tammie K Heller
(74) *Attorney, Agent, or Firm*—Faegre & Benson LLP (57) ABSTRACT

A lead for sensing and pacing a left ventricle of the heart includes a lead body having a proximal portion and a distal portion, a lumen extending through the lead body, a conductor extending through the lead body from the proximal end to the distal end and an electrode disposed on the distal portion of the lead body and electrically coupled to the conductor. A distal tip of the lead body is continuously deflectable upon advancement and withdrawal of a stylet through the lumen at the distal portion to access a selected branch of the coronary sinus. The distal tip of the lead body may be offset before or after continuously deflecting the distal tip.

22 Claims, 8 Drawing Sheets

U.S. PATENT DOCUMENTS

| | | |
|---|---|---|
| 6,076,019 A | 6/2000 | Rutten |
| 6,094,596 A | 7/2000 | Morgan |
| 6,144,882 A | 11/2000 | Sommer et al. |
| 6,321,123 B1 | 11/2001 | Morris et al. |
| 6,363,288 B1 | 3/2002 | Bush et al. |
| 6,385,492 B1 | 5/2002 | Ollivier et al. |
| 6,928,313 B2 * | 8/2005 | Peterson .................... 600/374 |
| 6,968,237 B2 | 11/2005 | Doan et al. |
| 2002/0143380 A1 | 10/2002 | Dahl et al. |
| 2002/0169484 A1 * | 11/2002 | Mathis et al. .................. 607/9 |
| 2003/0220677 A1 | 11/2003 | Doan et al. |

FOREIGN PATENT DOCUMENTS

| | | |
|---|---|---|
| WO | 02/18006 | 3/2002 |

* cited by examiner

LEFT VENTRICULAR LEAD SHAPES

TECHNICAL FIELD

The present invention relates to medical devices and methods for accessing an anatomical space of the body. More specifically, the invention relates to a lead for having improved stability for accessing the left ventricle of the heart and a method for implanting the lead.

BACKGROUND

Implantable medical devices for treating irregular contractions of the heart with electrical stimuli are well known in the art. Some of the most common forms of such implantable devices are defibrillators and pacemakers. Various types of electrical leads for defibrillators and pacemakers have been suggested in the prior art.

A broad group of those cardiac leads may be characterized by the fact that they are placed transvenously. These leads are introduced into the patient's vasculature at a venous access site and travel through veins to the locations where the leads' electrodes will implant in or otherwise contact coronary tissue. One large subfamily of the group of transvenously-placed leads are those that are implanted in the endocardium (the tissue lining the inside of the heart) of the right atrium or ventricle. Another subfamily of the group of transvenously-placed leads are those that are placed in the branch vessels of the coronary venous system to stimulate the left ventricle.

In general, directing a lead through a patient's vasculature can be a challenging proposition for a cardiac physician. For example, those leads that are placed in a branch vessel of the coronary venous system must be navigated to the right atrium of the heart, through the coronary sinus ostium, through the coronary sinus, and then into a desired branch vessel. To assist in such lead placements, a physician will typically use a device such as a guide wire or catheter with a pre-formed bend at its distal end. By rotationally manipulating the proximal end of the device, the distal end of the device can be pointed in a preferred direction, for example, toward a branch entrance. After the device has been placed, a lead will then follow either over the guide wire or within the catheter to the electrode placement site.

On occasion, a physician might wish to deploy a lead without first navigating another device in advance to the electrode placement site. The flexible nature of leads, though, is such that they exhibit very little inchessteerability inches or distal response to proximal manipulation. One response to this problem is to deploy a lead with a stylet or guide wire (hereafter simply referred to as a stylet) residing in the lead's central lumen to provide shape and steerability to the lead. The stylet would then be removed when lead placement was achieved.

Another response is to pre-form the distal end of the lead with a curvature adapted to facilitate access of particular anatomic features, for example, branch veins of the coronary sinus. It can be difficult to properly align the distal end of the lead to the branch veins so as to take advantage of the distal curvature of the lead. There is a need in the art for a device and method for aligning the distal end of an electrical lead with desired anatomical features.

SUMMARY

In one embodiment, the present invention is an electrical lead for a left ventricle of the heart. The lead includes a lead body having a proximal portion and a distal portion, the distal portion having at least a first preformed curvature. One or more lumens extend through the lead body. One or more conductors extend through the lead body from the proximal end to the distal end. One or more electrodes are disposed on the distal portion of the lead body and is electrically coupled to the conductor. The distal portion of the lead body is continuously deflectable upon advancement and withdrawal of a stylet through the lumen at the curved region.

In another embodiment, the present invention is an electrical lead for a left ventricle of the heart. The lead includes a lead body having a proximal portion and a distal portion, the distal portion having at least a first preformed curvature. One or more lumens extend through the lead body. One or more conductors extend through the lead body from the proximal end to the distal end. One or more electrodes are disposed on the distal portion of the lead body and is electrically coupled to the conductor. The distal portion of the lead body is continuously deflectable upon advancement and withdrawal of a stylet through the lumen at the curved region. The lead further includes an offset feature on the lead body.

In yet another embodiment, the present invention is a method of implanting a lead in the left ventricle of the heart. A stylet is pre-loaded into a lumen of the lead. The stylet and lead are advanced into a coronary sinus. A distal tip of the lead is smoothly deflected by advancing and withdrawing the stylet through a distal portion of the lead. A selected branch of the coronary sinus is accessed with the distal tip and the distal tip of the lead is seated in the selected branch of the coronary sinus.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
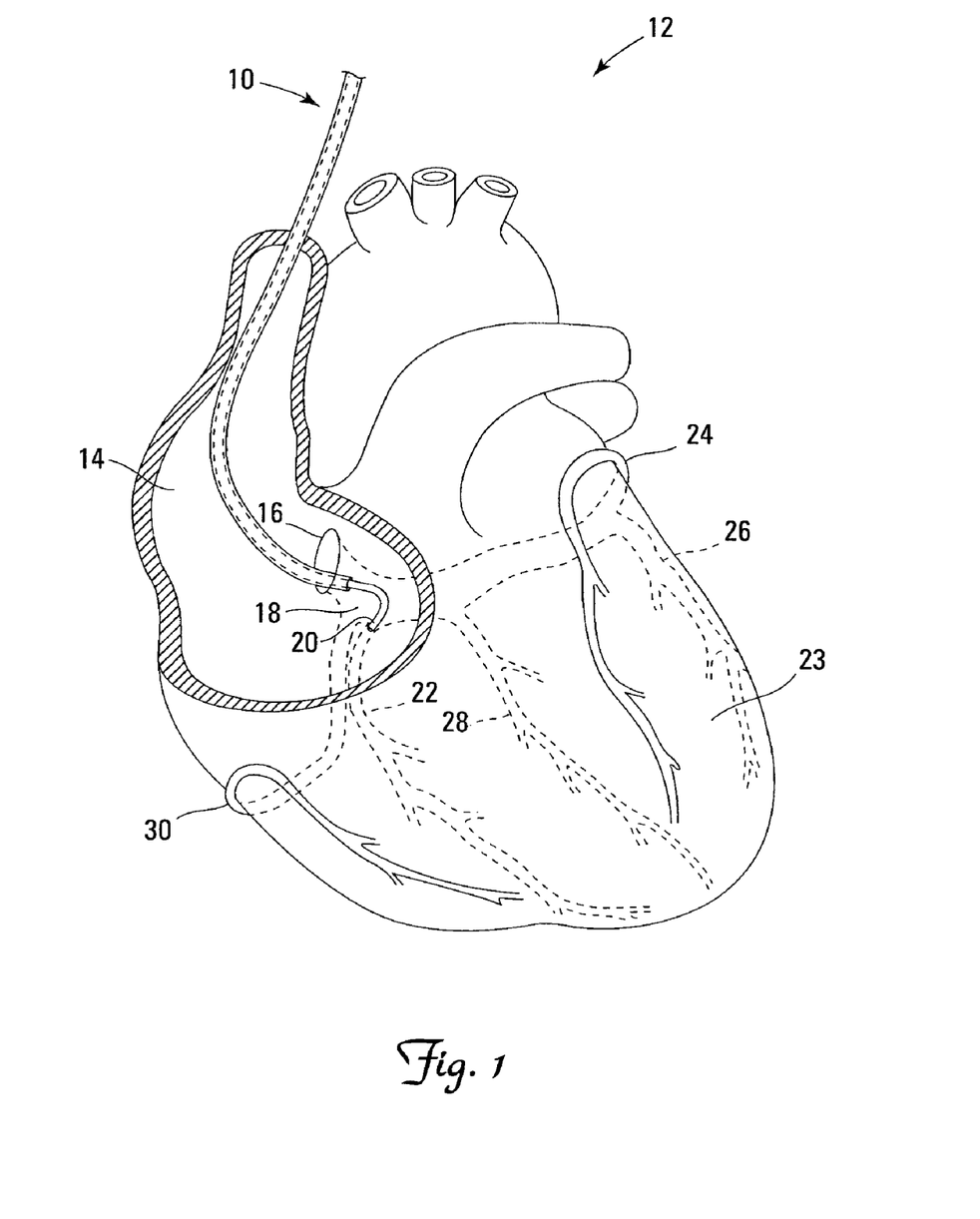
FIG. 1 shows a sectional view of a electrical lead accessing a portion of the vasculature according to one embodiment of the present invention.

FIG. 1 is a perspective view of an electrical lead 10 accessing a heart 12 via the right atrium 14. The electrical lead 10 extends into the right atrium 14, through the coronary sinus ostium 16 and into the coronary sinus 18. A distal tip 20 of the electrical lead 10 is shown accessing the middle cardiac vein 22, a branch vein of the coronary sinus 18. Once positioned in the middle cardiac vein 22, the electrical lead 10 can be used to sense the electrical activity of the heart 12 or to apply a stimulating pulse to the heart 12 at the left ventricle 23. In other embodiments, the electrical lead 10 is operable to access any other branch vein of the coronary sinus 18 as is known in the art of cardiac function management. For example, it may be used to access the great cardiac vein 24, the left marginal vein 26, the left posterior ventricular vein 28 or the small cardiac vein 30.

Figure 2:
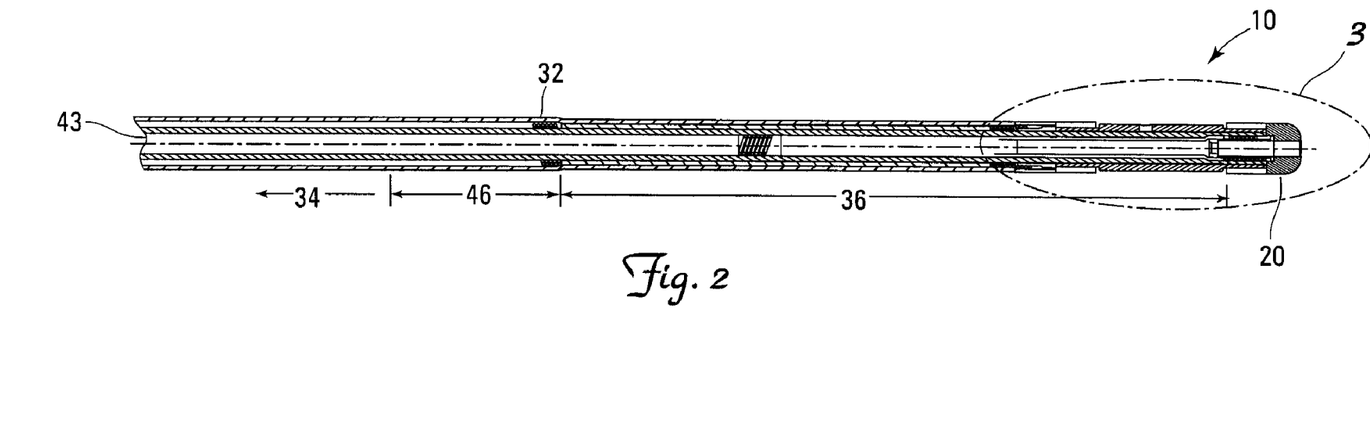
FIG. 2 shows a cross-sectional view of an exemplary implantable lead in a straightened configuration that can be used in relation to embodiments of the present invention.
Figure 3:
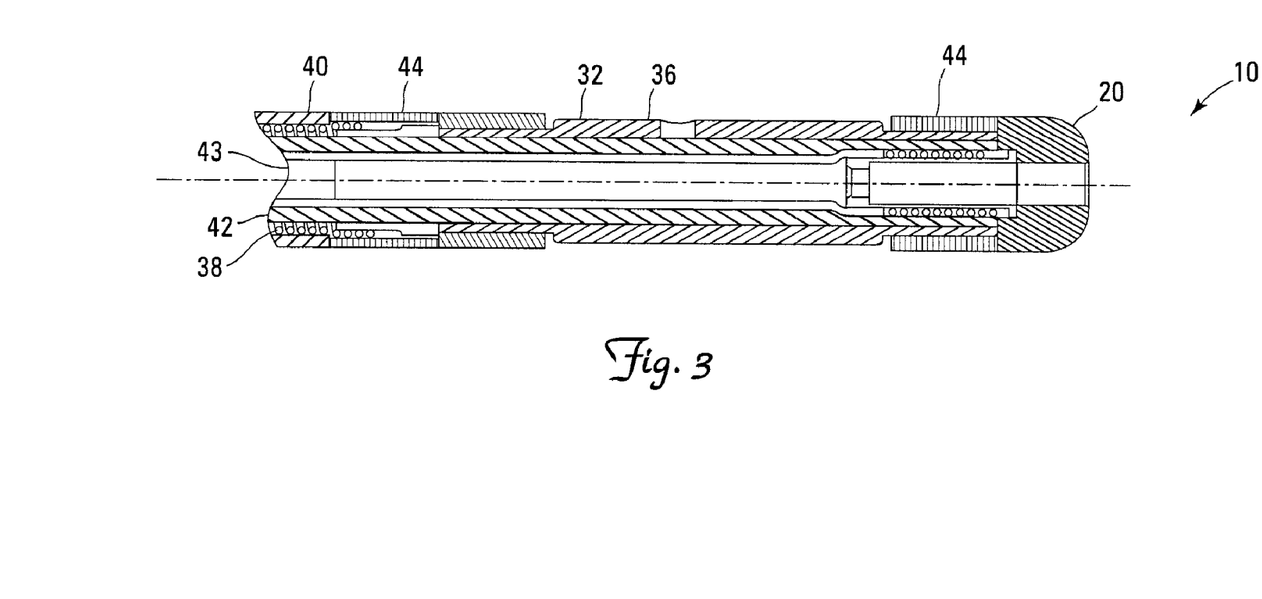
FIG. 3 shows an expanded cross-sectional view of the distal portion of the lead shown in FIG. 2.

FIGS. 2 and 3 are detailed sectional views of the electrical lead 10 according to one embodiment of the present invention. In the illustrated embodiment, the electrical lead 10 includes an elongated flexible lead body 32 constructed of a conductive coil 38 sandwiched between an outer sheath 40 and an inner sheath 42. The inner sheath 42 defines a lumen 43 that is open at the distal tip 20. One or more electrodes 44 are positioned along the lead body 32 and are in electric communication with the coil 38. A lead in accordance with the present invention, however, is not limited to the configuration previously described. The lead 10, rather, may have any configuration as is known in the art. For example, the lead may include a fewer or greater number of lumens 44, a non-coiled conductor 38, or other features as are known in the art. In another example, the lead 10 may be bipolar in which each electrode 44 would be in electric communication with a separate conductor 38.

The lead body 32 has a proximal portion 34 and a distal portion 36. The distal portion 36, shown in FIG. 3, terminates at the distal tip 20, while the proximal portion 34 forms the remainder of the lead body 32. The proximal portion 34 is operable to manipulate the distal portion 36 through the vasculature to position the distal tip 20 into a branch of the coronary sinus 20 so that the electrode(s) 44 make contact with the heart 12 at the left ventricle 23.

Figure 4:
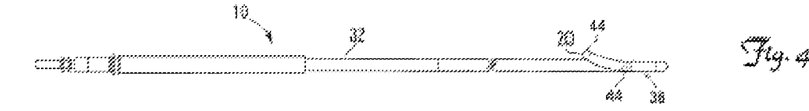
FIG. 4. shows a front schematic view of the lead of FIG. 2 in its biased configuration.
Figure 5:
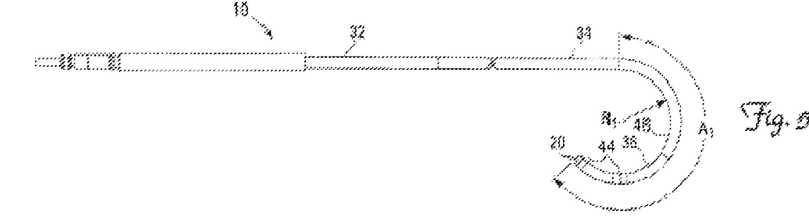
FIG. 5 shows a side schematic view of the lead of FIG. 4.
Figures 5A, 6:
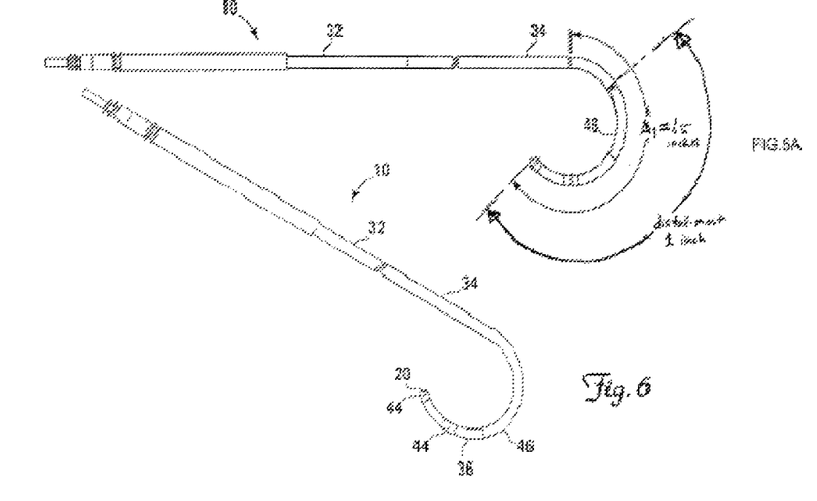
FIG. 5A shows a side schematic view of an example of the lead shown in FIG. 4.
FIG. 6 shows a perspective schematic view of the lead of FIG. 4.

The electrical lead 10 is shown in FIGS. 2 and 3 as generally straight or linear so as to render the details of the lead body 32 with greater clarity. However, in accordance with the present invention, the proximal portion 34 of the electrical lead 10 is generally straight or unbiased while the distal portion 36 is curved or biased, as is shown in FIGS. 4-6. The curvature of the distal portion 36 facilitates accessing branch veins of the coronary sinus 18. The distal portion 36 of the electrical lead 10 may have a variety of configurations in order to facilitate access to particular branch veins, or to accommodate unusual patient heart anatomy due to disease or other abnormality.

As shown in FIG. 5, the curvature of the distal portion 36 is primarily in two dimensions, or within a single plane. According to another embodiment, however, as shown in FIG. 4, the curvature of the distal portion 36 is non-planar.

The curvature of the distal portion 36 of the electrical lead 10 is definable in terms of a radius of curvature $R_1$ and an arc length $A_1$. In the embodiment shown in FIGS. 4-6, $R_1$ is constant through the distal portion 36 of the lead body 32. The radius of curvature $R_1$ may be sized up or down according to the anatomy of the patient and depending upon which branches of the coronary venous system are to be accessed. For example, in one embodiment, the radius of curvature $R_1$ of the distal portion 36 of the lead body 32, though constant in any one lead, is from about 0.2 inches to about 0.8 inches. In one embodiment, $R_1$ is about 0.4 inches+/−0.04 inches.

The arc length $A_1$ may also be sized up or down according to the anatomy of the patient and depending upon which branches of the coronary venous system are to be accessed. For example, in one embodiment, the radius of curvature $A_1$ of the distal portion 36 of the lead body 32 is from about 0.75 inches to about 3 inches. In one embodiment, $A_1$ is about 1.5 inches+/−0.5 inches, as shown in FIG. 5A.

The distal end 36 of the lead body 32 may be pre-formed with the radius of curvature $R_1$ according to a variety of means known in the art. For example, the sheaths 40 and/or 42 may be heat-set or the conductor 38 may be plastically deformed to impart a curvature at the distal portion 36.

Various regions of the lead body 32 may exhibit increased stiffness or resistance to bending. In one embodiment, the proximal portion 34 of the lead body 32 has an increased stiffness relative to the distal portion 36. A transition region 46 is formed in the lead body 32 where the lead body 32 transitions from the stiffer proximal portion 34 to the less stiff distal portion 36. However, the regions of varying stiffness do not necessarily correspond directly to the proximal portion 34 and distal portion 36. Thus, while in FIGS. 5 and 6, the transition region 46 is positioned between the proximal portion 34 and the distal portion 36, in other embodiments the transition region 46 may be formed anywhere along the distal-most about 1 inch to about 4 inches of the lead body 32. For example, the distal-most about 1 inch is indicated in FIG. 5. Furthermore, multiple transition regions 46 may be formed on a single lead having multiple regions of varying flexibility or stiffness.

Figure 8:
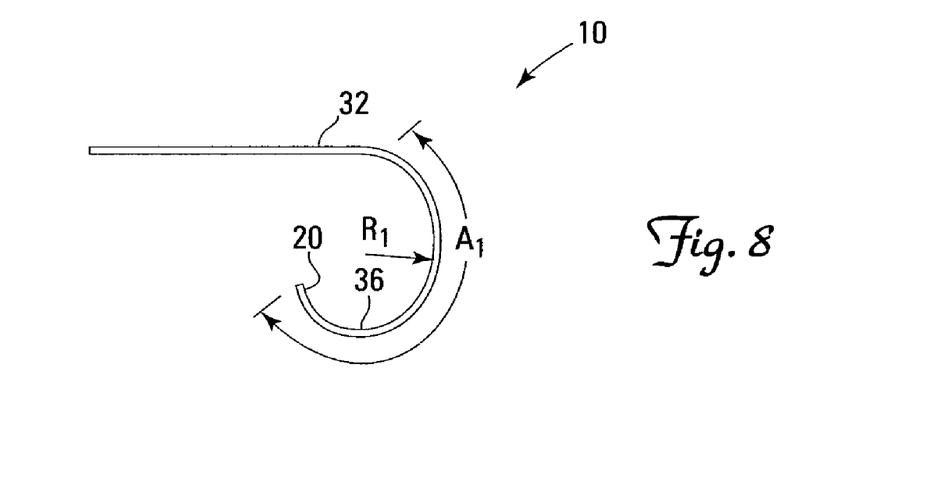
FIGS. 8-15 show side schematic views of a lead in accordance with various embodiment of the present invention.

FIGS. 8-15 show leads having different configurations in accordance with various embodiments of the present invention. As shown in FIG. 8, in one embodiment, the radius of curvature $R_1$ of the distal portion 36 of the lead body 32 is continuous and decreasing in a distal direction. This shape provides a variable, but continuous, tip deflection or angulation as the stylet 50 is inserted and withdrawn through the distal portion 36 of the lead body 32. In addition, the smaller distal radius provides improved electrode-tissue contact and access to acute branch takeoffs. The radius of curvature $R_1$ of the distal portion 36 of the embodiment shown generally in FIG. 8 can vary continuously anywhere from about 1.5 inches to about 0.2 inches in a proximal to distal direction, while the arc length $A_1$ of the distal portion 36 is from about 0.7 inches to about 3 inches. In one embodiment, $R_1$ is about 1.5 inches at the most proximal point of the distal portion 36 and about 0.2 inches at the most distal point of the distal portion 36.

Figure 9:
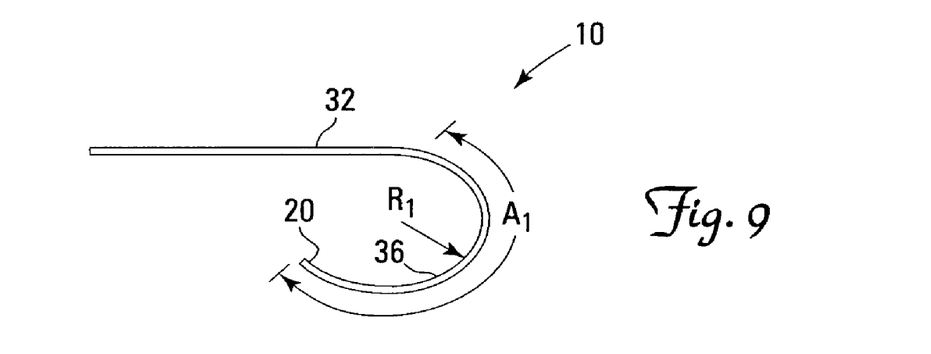

As shown in FIG. 9, in another embodiment, the radius of curvature $R_1$ of the distal portion 36 of the lead body 32 is continuous and increasing in a distal direction. This shape provides variable, but continuous, tip deflection or angulation as the stylet 50 is inserted and withdrawn through the distal portion 36 of the lead body 32. The larger distal radius reduces the likelihood of the distal tip 20 prolapsing, and is also useful for accessing gradual or obtuse branch takeoffs. The smaller proximal radius provides improved fixation relative to the larger radius. Finally, the continuous, increasing radius of curvature ensures that the smaller radius portion of the distal portion 36 is supported by a stiffer (i.e., more proximal) portion of the stylet 50, while the larger radius portion of the distal portion 36, which is less difficult to straighten out, is supported by a more flexible (i.e., more distal) portion of the stylet 50.

As used herein, "continuous" refers to the maximum change in unit of radius of curvature per unit of arc length. In one embodiment, the radius of curvature of the distal portion increases or decreases by no more than 0.5 mm per 1 mm along the arc length of the lead. In another embodiment, the radius of curvature of the distal portion increases or decreases by no more than 0.2 mm per 1 mm along the arc length of the lead 10.

FIGS. 10-14 show various embodiments of a lead according to the present invention in which the distal portion 36 of the lead body 32, while still having a continuous radius of curvature, is offset from the proximal portion 34. The features shown on the following embodiments may be incorporated into any of the embodiments previously discussed.

Figure 10:
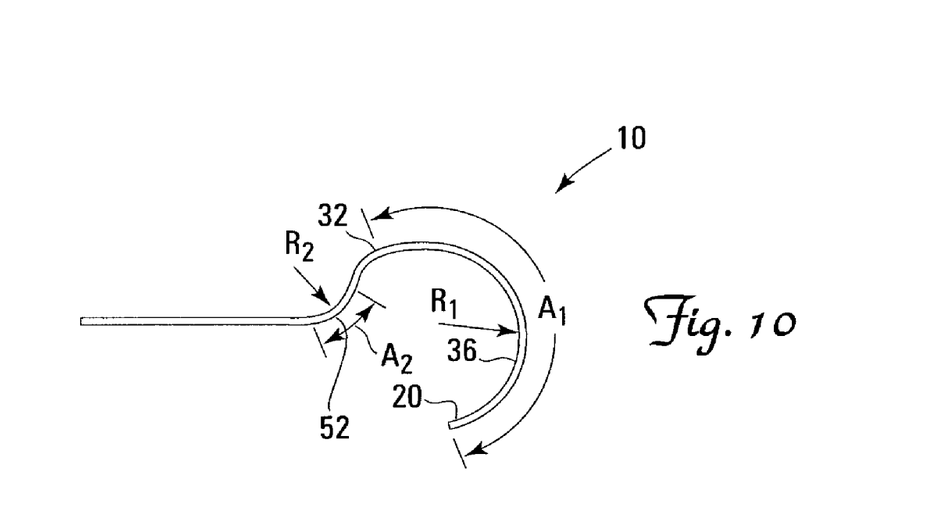

FIG. 10 shows one embodiment, in which the electrical lead 10 includes an offset feature 52 proximal to the distal portion 36. The offset feature 52 comprises a region of the lead body 32 that is curved in the opposite direction as the distal portion 36, or has a reverse curvature. The offset feature 52 causes the distal portion 36 to be shaped like a question mark. Any of the embodiments of the electrical lead 10 as previously described can include the offset feature 52. In one embodiment, the radius of curvature $R_1$ of the distal portion 36 is, or varies within, from about 0.2 inches to about 1.5 inches and the arc length $A_1$ of the distal portion 36 is from about 0.7 inches to about 3 inches. The offset feature 52 has a radius of curvature $R_2$ of from about 0.2 inches to about 1.5 inches and an arc length $A_2$ of from about 0.3 inches to about 1.5 inches. The continuous radius of the distal portion 36 provides a continuous or smoothly variable tip 20 deflection or angulation when the stylet 50 is inserted and withdrawn. The offset feature 52 provides more points of contact between the electrical lead 10 and the vessel in which the electrical lead 10 is located for improved fixation.

Figure 11:
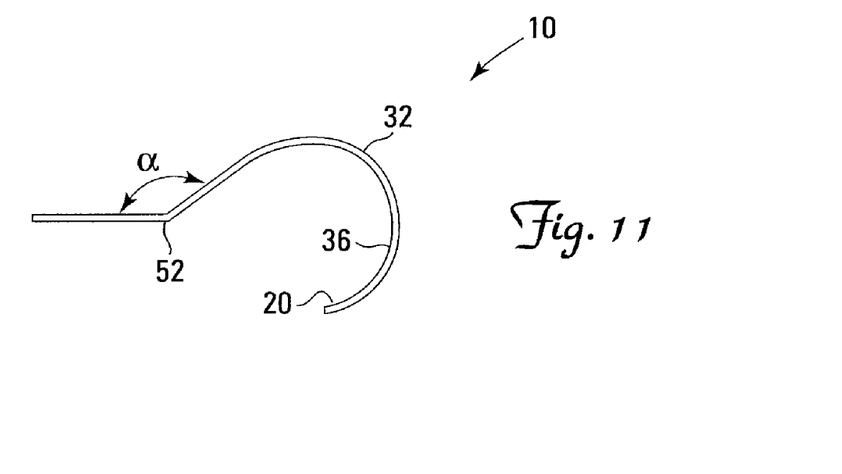

FIG. 11 shows another embodiment of the electrical lead 10. The electrical lead 10 of FIG. 11 is similar in many respects to the embodiment shown in FIG. 10. In the embodiment of FIG. 11, however, the offset feature 52 is a region of the lead body 32 that is angularly offset, or elbow shaped, rather than curved, as shown in FIG. 10. An angle α of the offset feature 52 can vary from about 90° to about 160°.

Figure 12:
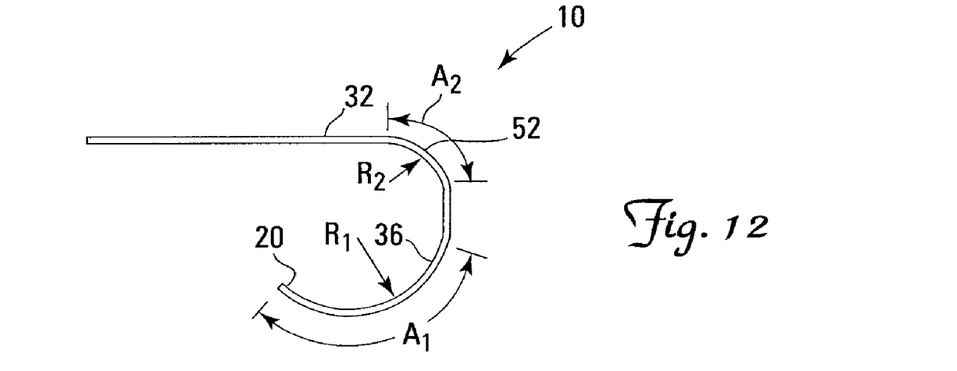

FIG. 12 shows another embodiment of the electrical lead 10, in which the offset feature 52 is a secondary curvature of the lead body 32 proximal to the distal portion 36. The offset feature 52 has a smaller radius of curvature than the distal portion 36 and is separated from the curvature of the distal portion 36 by a linear segment of the lead body 32. The distal radius of curvature $R_1$ is, or can vary within, from about 0.4 inches to about 1.5 inches. An arc length $A_1$ of the distal portion is from about 0.5 inches to about 2.0 inches. The offset feature 52 has a radius of curvature $R_2$ of from about 0.2 inches to about 0.6 inches and an arc length $A_2$ of from about 0.3 inches to about 1 inch. The continuous radius of curvature at the distal portion 36 provides smoothly variable tip 20 deflection or angulation when the stylet 50 is inserted and withdrawn. The larger radius at the distal portion 36 reduces the likelihood of the distal tip 20 prolapsing, and is also useful for accessing gradual or obtuse branch takeoffs. The smaller radius of the offset feature 52 provides improved fixation of the electrical lead 10 within the vessel relative to the larger radius of the distal portion 36. Finally, the smaller radius portion at the offset feature 52 is supported by a stiffer (i.e., more proximal) portion of the stylet 50, while the larger radius portion of the distal portion 36, which is less difficult to straighten out, is supported by the more flexible (i.e., more distal) portion of the stylet 50.

Figure 13:
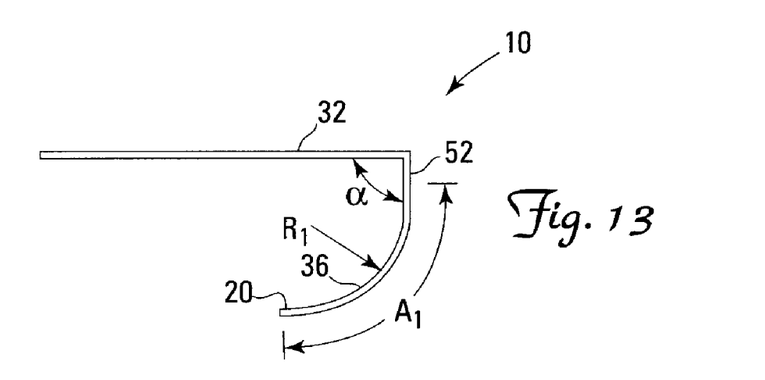

FIG. 13 shows another embodiment of the electrical lead 10. The electrical lead 10 of FIG. 13 is similar in many respects to the embodiment shown in FIG. 12. In the embodiment of FIG. 13, however, the offset feature 52 is a region of the lead body 32 that is angularly offset, or elbow shaped, in the same direction as the curvature of the distal portion 36, rather than being curved, as shown in FIG. 12. An angle α of the offset feature 52 can vary from about 90° to about 150°. The offset feature 52 causes the tip 20 to pivot or deflect sharply upon withdrawal or insertion of the stylet 50 through the offset feature 52, but to have a smoothly variable pivoting or deflecting action as the stylet 50 is inserted and withdrawn through the distal portion 36.

Figure 14:
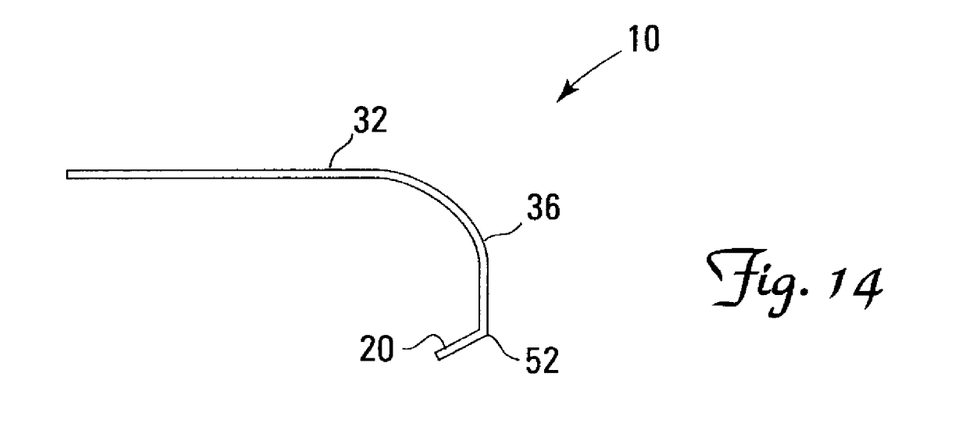

FIG. 14 shows another embodiment of the electrical lead 10, in which the offset feature 52 is an angular or elbow shaped region of the lead body 32 distal to the curvature of the distal portion 36. The offset feature 52 is at or just slightly proximal to the distal tip 20 of the electrical lead 10. This shape provides smoothly variable tip deflection or angulation as the stylet 50 is inserted or withdrawn through the distal portion 36. The unsupported offset region 52, however, points the distal tip 20 inwardly, providing better contact between the electrodes 44 and the tissue of the heart 12.

Figure 15:
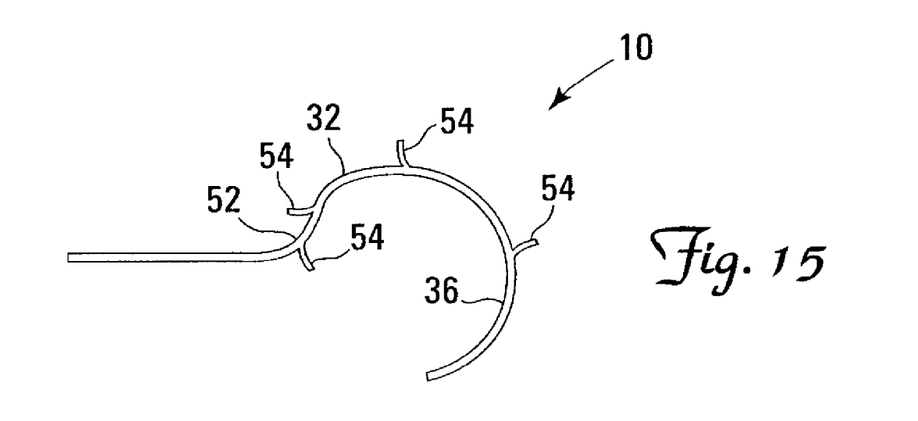

FIG. 15 shows another embodiment in which the electrical lead 10 is provided with a stability feature 54 at the distal portion 36 of the lead body 32. In the present embodiment, a plurality of the stability features 54 are positioned along outer tangents of the curvature of the distal portion 36 and offset feature 52. The stability features 54 protrude from the lead body 32, increasing the friction force with which the lead must overcome to be moved or dislodged. The stability features 54 also help control the ability to steer the distal tip 20 of the lead 10. In the present embodiment, the stability features 54 are tines. The stability features 54, however, may have any other protruding shape, including silicon tines, pins, leaf springs and the like. Further, any of the embodiments of the electrical lead 10 previously discussed can include stability features 54.

Figure 7:
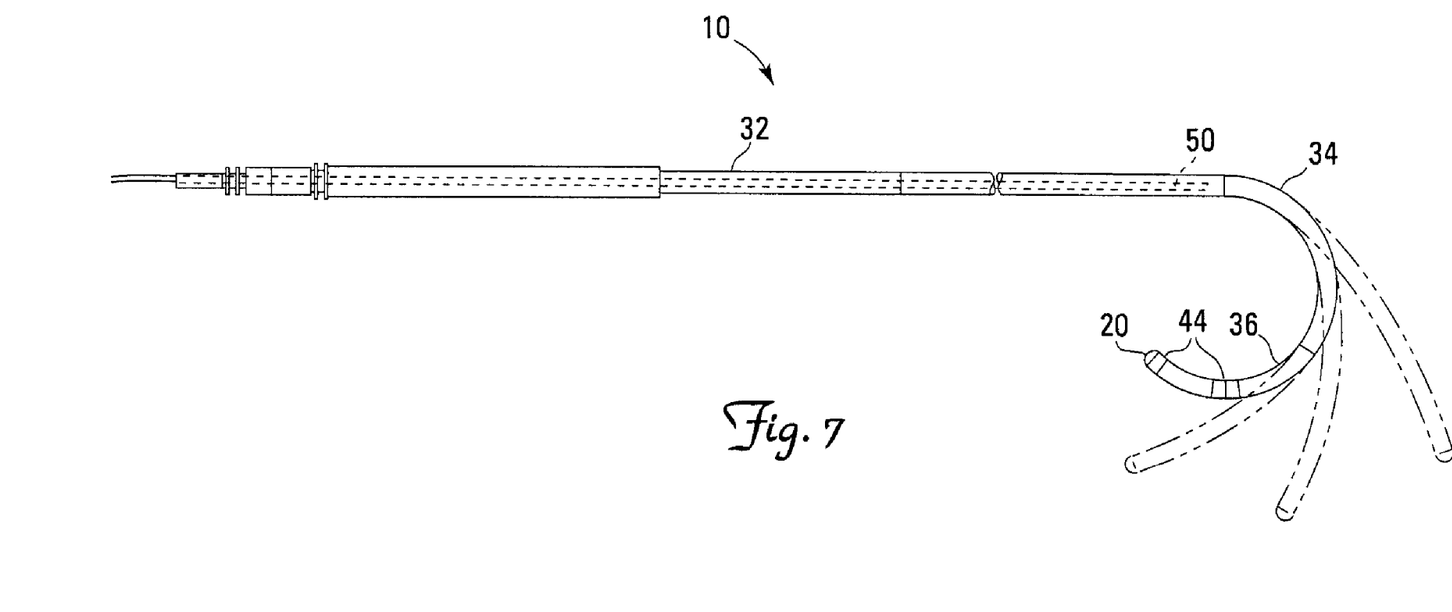
FIG. 7 shows a side schematic view of the lead of FIG. 2 assembled with a stylet.

The electrical lead 10 is advanced through the vasculature to access a branch vessel of the coronary sinus 18 via the coronary sinus ostium 16. A stylet 50, as shown in FIG. 7, may be employed to provide support, shape and deflection to the electrical lead 10 as the electrical lead 10 is advanced. Because the stylet 50 is more rigid than the electrical lead 10, the electrical lead 10 partially or completely bends in conformity with the shape of the stylet 50. The stylet 50 may be straight or may include biased or curved regions. The electrical lead 10 thereby partially or completely takes on the shape of the stylet 50.

Figure 16:
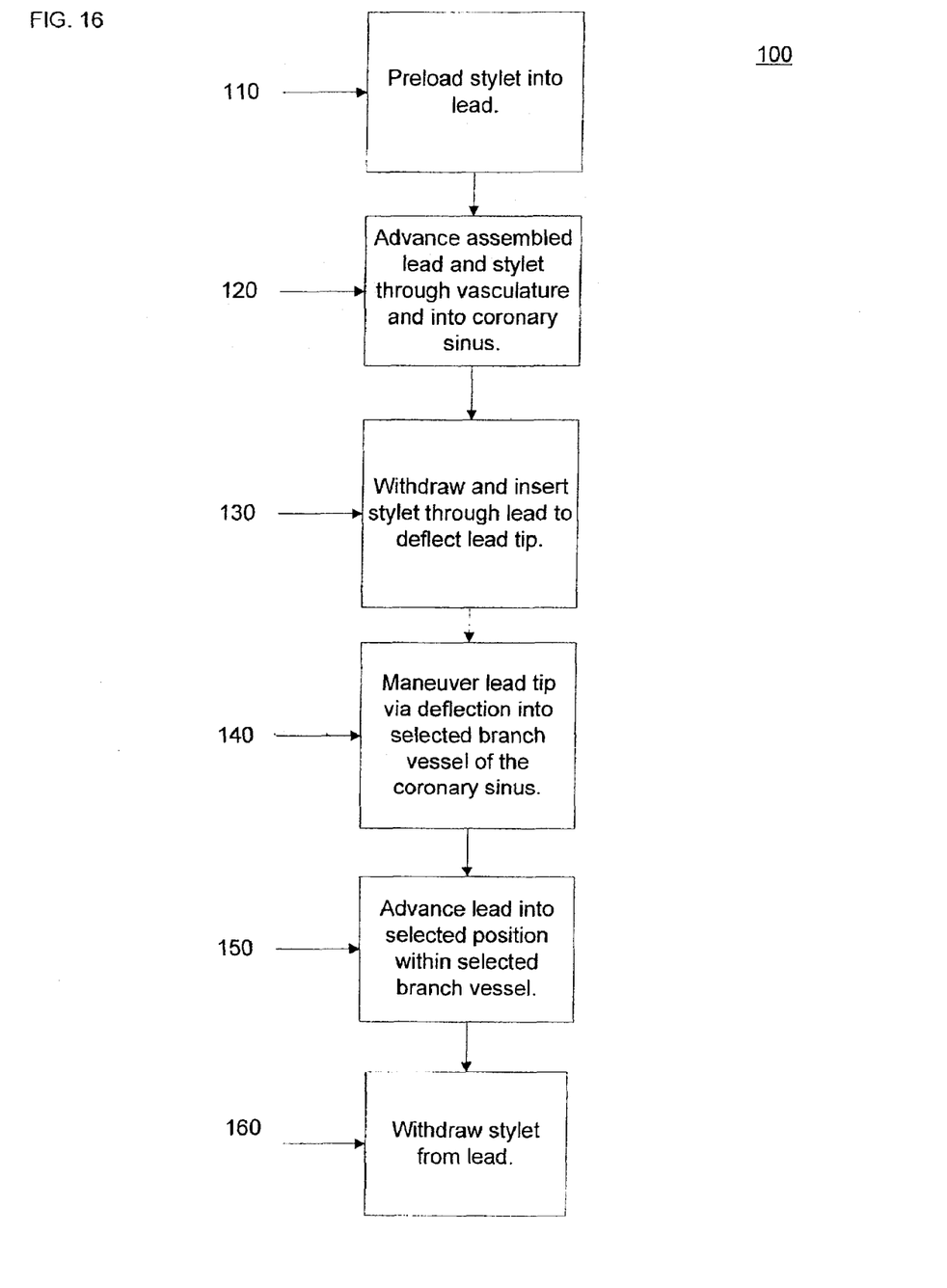
FIG. 16 is a block diagram showing a method of accessing a branch vessel of the coronary sinus with a lead according to one embodiment of the present invention.

FIG. 16 is a block diagram illustrating a method 100 of accessing a branch vessel of the coronary sinus 18 with the electrical lead according to one embodiment of the invention. The stylet 50 is preloaded into the lumen 43 as shown in FIG. 7 (block 110). The assembled stylet 50 and electrical lead 10 are advanced through the patient's vasculature to the right atrium 14, through the coronary sinus ostium 16 and into the coronary sinus 18 (block 120). As the electrical lead 10 is advanced towards the branches of the coronary sinus 18, the stylet 50 is withdrawn slightly so that the distal portion 36 of the lead body 32 is unsupported by the stylet 50 (block 130). The unsupported lead body 32 reverts to the preformed curvature at the distal portion 36. As shown in dashed lines in FIG. 7, withdrawal and advancement of the stylet 50 through the lumen 43 at the distal portion 36 causes the distal tip 20 of the electrical lead 10 to deflect relative to the proximal portion 34 of the lead body 32. This deflection or angulation of the distal tip 20 is employed to maneuver the electrical lead 10 through the vasculature and to access a selected branch of the coronary sinus 20 (block 140). Upon accessing the selected branch, the electrical lead 10 is advanced distally to seat the electrodes 44 within the branch vessel in contact with the heart 12 (block 150). After the distal tip 20 and electrodes 44 are positioned at an electrode placement site, the stylet 50 is withdrawn, leaving the electrical lead 10 implanted in the heart 12 for pacing and sensing of the left ventricle 23 (block 160).

The shape of the electrical lead 10 according to the present invention provides for a more easily maneuverable lead for accessing the branches of the coronary sinus 18. Specifically, because the radius of curvature of the distal portion 36 is continuous, the distal tip 20 pivots smoothly, or has a continuous tip 20 deflection or angulation, as the stylet 50 is advanced and withdrawn through the distal portion 36. Breaks, jerky motions and abrupt positional changes of the distal tip 20 are therefore avoided. The deflection or angulation of the tip 20 is therefore more predictable, providing for a more efficient insertion procedure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electrical lead assembly for a left ventricle of the heart, the lead assembly comprising:
    a lead with a lead body having a proximal unbiased region and a continuously deflectable preformed curvature extending from the unbiased region, the lead body further having a stiff proximal portion, a flexible distal portion that is more flexible than the stiff proximal portion, and a transition portion between the flexible distal portion and the stiff proximal portion, the flexible distal portion including a distal tip of the lead body, the continuously deflectable preformed curvature curved in one direction through a single plane, the lead having a lumen extending through the lead body, the lumen having a distal end and a proximal end and a first length from the distal to the proximal end, the lead further having a conductor extending through at least a portion of the lead body and an electrode disposed on the distal portion of the lead body and electrically coupled to the conductor, wherein a portion of the stiff proximal portion extends into the continuously deflectable preformed curvature such that the stiff proximal portion provides support to at least a portion of the continuously deflectable preformed curvature; and
    a stylet that is sized to fit within the lumen, the stylet having a proximal portion, a distal portion with increased flexibility relative to the proximal portion, and a second length from a distal end to a proximal end of the stylet, the second length being at least as long as the first length;
    wherein the stylet distal portion has a first stiffness and the lead body distal portion has a second stiffness, the first stiffness being sufficiently stiff relative to the second stiffness to straighten the continuously deflectable preformed curvature from a first curved configuration to a second curved configuration when the stylet distal end is positioned in the lumen adjacent the lead body distal end, wherein the first and second curved configurations are shaped to facilitate access to branch vessels of the coronary sinus.

2. The lead assembly of claim 1 wherein the continuously deflectable preformed curvature has a constant radius of curvature.

3. The lead assembly of claim 2 wherein the continuously deflectable preformed curvature has a radius of curvature of about 0.4 inches and an arc length of the lead body is about 1.5 inches.

4. The lead assembly of claim 1 wherein the continuously deflectable preformed curvature has a decreasing radius of curvature in a distal direction.

5. The lead assembly of claim 4 wherein the continuously deflectable preformed curvature has a radius of curvature that varies within about 0.2 inches to about 1.5 inches and an arc length from about 0.7 inches to about 3 inches.

6. The lead assembly of claim 1 wherein the continuously deflectable preformed curvature has an increasing radius of curvature in a distal direction.

7. The lead assembly of claim 6 wherein the continuously deflectable preformed curvature has a radius of curvature that varies within about 0.2 inches to about 1.5 inches and an arc length from about 0.7 inches to about 3 inches.

8. The lead assembly of claim 1 wherein the transition portion is located within the distal most about 1 inch to about 4 inches of the lead body.

9. The lead assembly of claim 1 further comprising an offset feature.

10. The lead assembly of claim 1, further comprising a steering feature.

11. The lead assembly of claim 1, wherein the continuously deflectable preformed curvature has a maximum change of 0.5 mm of radius of curvature per 1 mm of arc length.

12. The lead assembly of claim 1, wherein the distal and proximal portions of the stylet are located along the stylet and the continuously deflectable preformed curvature is located along the lead body such that the stylet can be positioned in the lumen with a proximal portion of the preformed curvature supported by the stiff proximal portion of the stylet while a distal portion of the curvature is supported by the flexible distal portion of the stylet.

13. A lead assembly for a left ventricle of the heart, the lead assembly comprising:
    a stylet having a distal end and a proximal end and a first length between the distal and proximal ends, the stylet further having a proximal portion and a distal portion with increased flexibility relative to the proximal portion, the distal portion being a first distance from the stylet distal end; and
    a lead with a lead body having a proximal unbiased region, an offset feature distal of the unbiased region, and a preformed curvature distal of the offset feature, the lead body further having a stiff proximal portion, a flexible distal portion that is more flexible than the stiff proximal portion and a transition portion between the flexible distal portion and the stiff proximal portion, the flexible distal portion including a distal tip of the lead body, the preformed curvature curved in one direction through a single plane, wherein the preformed curvature is continuously deflectable upon advancement and withdrawal of the stylet through the lumen at the distal portion, the lead having a lumen extending through the lead body, the lumen having a distal end and a proximal end and a second length from the distal to the proximal end, the first length being at least as long as the second length, the lead further having a conductor extending through at least a portion of the lead body, an electrode disposed on the distal portion of the lead body and electrically coupled to the conductor, wherein a portion of the stiff proximal portion extends into the preformed curvature such that the stiff proximal portion provides support to at least a portion of the preformed curvature;

wherein the distal and proximal portions of the stylet are located along the stylet and the preformed curvature and the offset feature of the lead body are located along the lead body such that the stylet can be positioned within the lumen with the stiff proximal portion of the stylet supporting the offset feature while the flexible distal portion of the stylet supports a portion of the preformed curvature; and wherein the stylet distal portion has a first stiffness and the lead body flexible distal portion has a second stiffness, the first stiffness being sufficiently stiff relative to the second stiffness to straighten the preformed curvature from a first curved configuration to a second curved configuration when the stylet distal end is positioned in the lumen adjacent the lead body distal end, wherein the first and second curved configurations are shaped to facilitate access to branch vessels of the coronary sinus.

14. The lead assembly of claim 13 wherein the offset feature is a region of the lead body proximal to the distal portion that curves in the opposite direction as the preformed curvature.

15. The lead assembly of claim 13 wherein the offset feature is a region of the lead body proximal to the distal portion that is angled in the opposite direction as the preformed curvature.

16. The lead assembly of claim 13 wherein the offset feature is a region of the lead body proximal to the distal portion that is angled in the same direction as the preformed curvature.

17. The lead assembly of claim 13 wherein the offset feature is a region of the lead body proximal to the distal portion that is curved in the same direction as the distal portion and has a smaller radius of curvature than the preformed curvature.

18. The lead assembly of claim 13 wherein the offset feature is a region of the lead body adjacent a distal tip of the lead body that is angled in the same direction as the curvature of the preformed curvature.

19. The lead assembly of claim 13, wherein the continuously deflectable preformed curvature has a maximum change of 0.5 mm of radius of curvature per 1 mm of arc length.

20. The lead assembly of claim 13 wherein the preformed curvature has a constant radius of curvature.

21. The lead assembly of claim 13 wherein the preformed curvature has a decreasing radius of curvature in a distal direction.

22. The lead assembly of claim 13 wherein the preformed curvature has an increasing radius of curvature in a distal direction.

* * * * *